(12) United States Patent
Vickerson et al.

(10) Patent No.: US 9,844,223 B2
(45) Date of Patent: Dec. 19, 2017

(54) HERMETIA ILLUCENS FRASS PRODUCTION AND USE IN PLANT NUTRITION AND PEST MANAGEMENT

(71) Applicant: Enterra Feed Corporation, Vancouver (CA)

(72) Inventors: Andrew Vickerson, Vancouver (CA); Reed Radley, Vancouver (CA); Brad Marchant, Vancouver (CA); Oliver Kaulfuss, New Westminster (CA); Todd Kabaluk, Harrison Hot Springs (CA)

(73) Assignee: ENTERRA FEED CORPORATION, Langley, BC (CA)

( * ) Notice: Subject to any disclaimer, the term of this patent is extended or adjusted under 35 U.S.C. 154(b) by 0 days.

(21) Appl. No.: 14/908,924

(22) PCT Filed: Jul. 31, 2014

(86) PCT No.: PCT/CA2014/050727
§ 371 (c)(1),
(2) Date: Jan. 29, 2016

(87) PCT Pub. No.: WO2015/013826
PCT Pub. Date: Feb. 5, 2015

(65) Prior Publication Data
US 2016/0219887 A1 Aug. 4, 2016

Related U.S. Application Data

(60) Provisional application No. 61/861,936, filed on Aug. 2, 2013.

(51) Int. Cl.
*A01N 63/02* (2006.01)
*A01M 1/10* (2006.01)

(52) U.S. Cl.
CPC ............ *A01N 63/02* (2013.01); *A01M 1/106* (2013.01)

(58) Field of Classification Search
None
See application file for complete search history.

(56) References Cited

U.S. PATENT DOCUMENTS

| | | | |
|---|---|---|---|
| 3,939,883 A | 2/1976 | Harrell | |
| 4,850,305 A | 7/1989 | Georgi | |
| 5,158,497 A | 10/1992 | Rossignol | |
| 5,759,224 A | 6/1998 | Olivier | |
| 6,244,213 B1 | 6/2001 | Tedders | |
| 6,391,620 B1 | 5/2002 | Olivier | |
| 6,397,782 B1 | 6/2002 | Cope | |
| 6,557,487 B1 | 5/2003 | Fleischmann | |
| 6,780,637 B2 | 8/2004 | Olivier | |
| 6,786,001 B1 | 9/2004 | Piper | |
| 6,938,574 B2 | 9/2005 | Zhang | |
| 8,322,305 B2 | 12/2012 | Chang | |
| 9,510,572 B2 | 12/2016 | Aldana et al. | |
| 2002/0177219 A1 | 11/2002 | Olivier | |
| 2003/0143728 A1 | 7/2003 | Olivier | |
| 2003/0233982 A1 | 12/2003 | Zhang | |
| 2008/0163541 A1 | 7/2008 | Harris | |
| 2011/0081452 A1 | 4/2011 | Hem | |
| 2011/0174222 A1 | 7/2011 | Lee | |
| 2011/0296756 A1 | 12/2011 | Zhang | |
| 2012/0187041 A1 | 7/2012 | Popa | |
| 2014/0020630 A1 | 1/2014 | Courtright | |

FOREIGN PATENT DOCUMENTS

| | | |
|---|---|---|
| CA | 2834412 | 11/2012 |
| CN | 201185612 Y | 1/2009 |
| CN | 102329155 A | 1/2012 |
| CN | 101889629 B | 9/2012 |
| WO | 2010/002188 | 1/2010 |
| WO | 2012/100077 | 7/2012 |
| WO | 2013/166590 | 11/2013 |

OTHER PUBLICATIONS http://eol.org/pages/345/overview—accessed Apr. 2017.*
https://en.wikipedia.org/wiki/Scarabaeidae—accessed Apr. 2017.*
ISR & Written Opinion from PCT/CA2013/000457 dated Aug. 2, 2013.
ISR & Written Opinion from PCT/CA2014/050727 dated Oct. 22, 2014.
ISR & Written Opinion from PCT/CA2015/050653 dated Sep. 29, 2015.
EESR from European Patent Application No. 13787121.6 dated Oct. 30, 2015.
Restriction Requirement from U.S. Appl. No. 14/397,679 dated Mar. 7, 2016.
Biopod: the future offood waste diversion and recycling, Black Soldier Fly Forum: Breeding BSF in captivity, Reply #22 'Re: not easy by earthtiger, Nov. 26, 2011 (Nov. 26, 2011), URL: httQ:/lthebioQod.co111/folUmlindex.QhQ?toQic=175.15.
Bradley, S. W. and Sheppard, D. C. 1984. House Fly Oviposition Inhibition by Larvae of Hermetia illucens, the Black Soldier Fly. Journal of Chemical Ecology, 19, 853.
Enterra Feed Corporation. CTVNews—"Bugs Life"—Enterra Feed Corporation. Nov. 4, 2013 (Apr. 11, 2013) [online video, retrieved on Oct. 2, 2014 (Feb. 10, 2014)]. Retrieved from the internet: <URL: http://www.enterrafeed.comlctv-news-bugs-lifevideo/> or from: <URL: http://www.youtube.comlwatch?v=VBHVg_tdTLM>.

(Continued)

*Primary Examiner* — Susan Hoffman
(74) *Attorney, Agent, or Firm* — Casimir Jones, S.C.

(57) ABSTRACT

Apparatus and methods are provided for producing insecticidal black soldier fly (BSF; *Hermetia illucens*) frass, and using the frass for nutritional and insect pest control activity in soils and/or on foliage. The methods include processes for using BSF frass to reduce damage to crops caused by wireworms (i.e., click beetle larvae, in the Elateridae family) and/or other Coleopteran (i.e., beetle) insect pests. Also provided is an insect trap comprising BSF frass.

14 Claims, 9 Drawing Sheets

(56) References Cited

OTHER PUBLICATIONS

Enterra Feed Corporation. Enterra Natural Fertilizer™ Product Specifications. Jul. 2014 (Jul. 2014) and Jun. 2013 (Jun. 2013) [online PDF document, retrieved on Oct. 2, 2014 (Feb. 10, 2014)]. Retrieved from the internet: <URL:http://enterrafeed.coml wp-contentiuploadsIN atural-Fertilizer. pdf>.

Erickson, M. C., M. Islam, C. Sheppard, J. Liao, and M. P. Doyle. 2004. Reduction of *Eschericia coli* 0157:H7 and *Salmonella enterica* serovar Enteritidis in chicken manure by larvae of the black soldier fly. J. Food Protection. 67: 685-690.

Foster, S.P. et al. Behavioral manipUlation methods for insect pest-management. Annual Review a/Entomology, 1997, vol. 42, pp. 123-146, ISSN: 0066-4170 (Print).

Furman, D. P., R. D. Young, and E. P. Catts. 1959. Hermetia illucens (Linnaeus) as a factor in the natural control of Musca domestica Linnaeus. J. Econ. Entomol. 52: 917-921.

Green, T.R. et al. Applied Biochemistry and Biotechnology, online Jan. 12, 2012 (Dec. 1, 2012), Mar. 2012 (Mar. 2012), vol. 166, No. 6, pp. 1381-1387.

Hogsette, J. A. 1985. New diets for production of house flies and stable flies (Diptera: *Muscidae*) in the laboratory. J. Econ. Entomol. 85: 2291-2294.

Larde, Biological Wastes 30 (1989) 11-19.

Larde, Biological Wastes 333 (1990) 307-310.

Liu, Q., Tomerblin, J. K., Brady, J. A., Sanford, M. R., and Yu, Z. 2008. Black Soldier Fly (Diptera: *Stratiomyidae*) Larvae Reduce *Escherichia coli* in Dairy Manure. Environ. Entomol. 37(6): 1525-1530.

Myers, et al. Environ. Entomol. 37(1): 11-15(2008).

Olivier, P. A. (2009) "Utilizing lower life forms for the bioconversion of putrescent waste." Black Soldier Fly Blog—Official Website.

Sheppard et al, Bioresource Technology 50 (1994) 275-279.

Sheppard et al, Black Soldier Fly Prepupae a Compelling Alternative to Fish Meal and Fish Oil, A Public Comment Prepared in Response to a Request by The National Marine isheries Service Nov. 15, 2007, http://www.aquacircle.org/images/pdfdokumenter/ udvikling/andre/amerika/Soldier fly_compelling_alternative_ NOAA-USDA.pdf.

Sheppard, D.C J.K.; J.K. Tomberlin, J.A. Joyce, B.C. Kiser & S.M. Sumner. 2002. Rearing Methods for the Black Soldier Fly (Diptera: *Stratiomyidae*). J. Med. Entomol. 39(4): 695-698.

St. Hilaire et al, Journal of the World Aquaculture Society, vol. 38, No. 1, Mar. 2007.

St. Hilaire et al, Journal of the World Aquaculture Society, vol. 38, No. 2, Jun. 2007.

Temple, W.D. et al. Use of Enterra Natural Fertilizer (Black Soldier Fly Larvae 1-20 Digestate) As a Soil Amendment. Enterra Feed Corporation, Nov. 2013 (Nov. 2013) [online PDF document, retrieved on Oct. 2, 2014 (Feb. 10, 2014)]. Rctrieved from the internet: <URL: http://www.certifiedorgank.bc.ca/programs/osdpll-172] rass_Research_Final%20Report.pdf>.

Tomberlin & Sheppard, Florida Entomologist, 84(4) Dec. 2001, 729-730.

Tomberlin, J. K., Alder, P. H., and Myers H. M. 2009. Development of the Black Soldier Fly (Diptera: *Stratiomyidae*) in Relation to Temperature. Environ. Entomo1.38: 930-934.

Tomberlin, J.K. & D.C. Sheppard. 2002. Factors Influencing Mating and Oviposition of Black Soldier Flies (Diptera: *Stratiomyidae*) in a Colony. J. Entomol. Sci. 37(4): 345-352.

Tomberlin, J.K., D. C. Sheppard & J.A. Joyce. 2002. Selected Life-History Traits of Black Soldier Flies (Diptera: *Stratiomyidae*) Reared on Three Artificial Diets. Ann. Entomol. Soc. Am. 95(3): 379-386.

Tossell, I. Conversation with David Suzuki leads to maggot-based animal feed. The Globe and Mail, Oct. 28, 2013 (Oct. 28, 2013) [online newspaper article, retrieved on Oct. 2, 2014 (Feb. 10, 2014)]. Retrieved from the internet: <URL: http://www. theglobeandmail.comlreport-on-business/small-business/starting-out!conversation-with-david-suzuki-leads-to-maggot-based-animal-feedlarticle15114182/>.

Zhang, et al. 2010. An artificial light source influences mating and oviposition of black soldier flies, *Hermetia illucens*. J. Insect Sci.10:1-7.

Newton, et al. Using the Black Soldier Fly, *Hermetia illucens*, As a Value-Added Tool for the Management of Swine Manure, Jun. 6, 2005, https://www.cals.ncsu.edu/waste_mgt/smithfield_projects/ phase2report05/cd,web%20files/A2.pdf.

Office Action from U.S. Appl. No. 14/397,679 dated May 13, 2016.

Notice of Allowance from U.S. Appl. No. 14/397,679 dated Aug. 12, 2016.

Office Action from European Application No. 13787121.6 dated Jun. 27, 2016.

\* cited by examiner

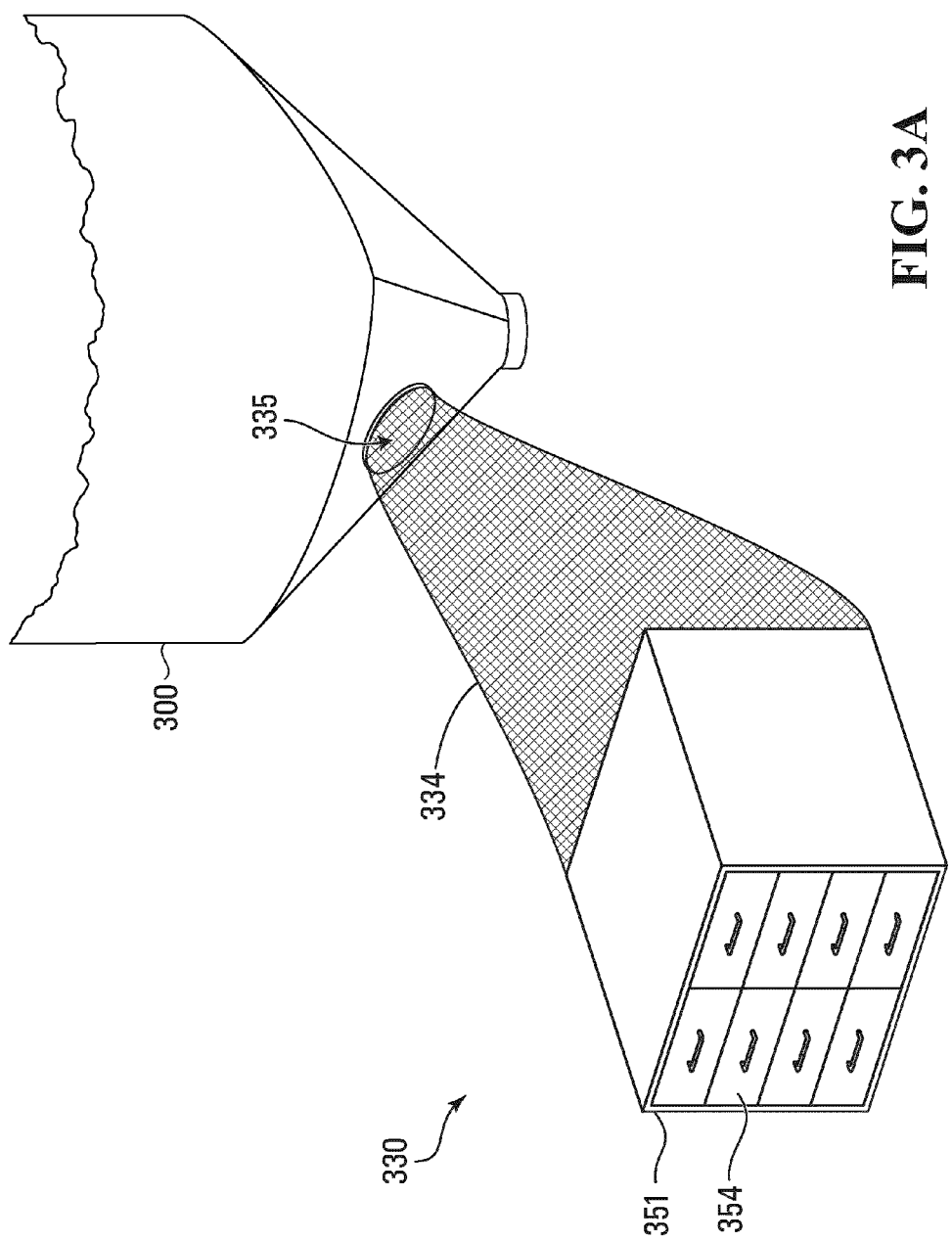

HERMETIA ILLUCENS FRASS PRODUCTION AND USE IN PLANT NUTRITION AND PEST MANAGEMENT

FIELD OF THE INVENTION

The invention relates to apparatus and methods for culturing Dipteran insects, particularly *Hermetia illucens* (commonly referred to as the black soldier fly), so as to produce byproducts having nutritional and pest control activity in soils and/or on plant foliage. In particular, the invention includes apparatus and methods for producing black soldier fly frass having nutritional and insecticidal pest control activities.

BACKGROUND OF THE INVENTION

Larvae of the black soldier fly (BSF; *Hermetia illucens*; as utilized herein, BSFs means black soldier flies) are well suited to converting organic waste products, such as fruit and vegetable matter (including coffee pulp), meat and fish, bread and grains, and manures, into market-valuable products, such as livestock (terrestrial or aquatic) feed or feed ingredients, pet food, food stuffs for human consumption, and plant growth supplements. Advantages of BSFs include the following: (i) BSFs are indigenous to the Americas and are now found in many parts of the world; (ii) BSF larvae grow on a wide variety of organic waste products; (iii) BSF larvae and prepupae are high in protein and fatty acid content and self-harvesting; (iv) BSF adults do not need food and are therefore are not known as a disease vector; (v) BSF larvae demonstrate anti-pathogenic qualities (Erickson, et al. 2004; Liu, et al. 2008); and (vi) BSF larvae produce stable colonies because they deter colonization from other insect species (Bradley and Sheppard, 1984) and can survive in a variety of environmental conditions.

As a member of the Family Stratiomyidae, the BSF goes through full metamorphosis during its lifespan. This includes the egg, larval, pupae and adult life cycle stages. Larvae will hatch from the egg stage after 48-72 hours and go through five instars (larval stages) before reaching the pupae stage. The first instar (L1) will molt into the second instar (L2) within 4-5 days and generally reach the pupae stage within a further 12-30 days, and for example, within 12-18 days, depending on temperature, humidity, type of feed, quantity of feed, frequency of feeding, mixture of feed ingredients, moisture of feed, starter diet, finishing diet and consistency of feed. Between the fifth instar (L5) and the pupae stage is the prepupae stage, where BSF larvae seek a drier environment, for example an environment that is less saturated or less than 100% moisture, to complete the metamorphosis stage of its life cycle. Accordingly, prepupae will crawl away from their "juvenile" feeding grounds, i.e., the organic wastes. This dispersal behavior translates into a "self-harvesting" mechanism which allows for a convenient collection of prepupae. Self-harvesting is further facilitated by the fact that BSF larvae are negatively phototactic and thus light can be used to encourage migration in desired directions upon user demand. The pupae stage generally lasts 9-20 days, and for example, 7-10 days depending on factors such as, for example, movement, proximity to other moving pupae, level of light, temperature and humidity, following which the adult fly will emerge. Adult BSFs mate and gravid female BSFs will lay eggs (i.e., "oviposit") for the next generation. The life span of an adult BSF is generally 6-15 days, and, for example, 7-10 days, depending on humidity (e.g., 50-90%) and/or temperature (e.g., 22-35° C.) and stored energy, such as quantities and profiles of protein and fat. The timeline for the aforementioned life cycle is approximate and depends on environmental conditions and food supply. For example, it has been reported that limited food supply can extend the larval period to 4 months (Furman et al., 1959).

Under appropriate conditions, gravid female BSF adults will oviposit eggs approximately 24-72 hours after mating. Eggs are generally oviposited in tight, narrow spaces, such as blocks of cardboard with flutes oriented in any direction. Females are typically attracted to oviposition sites with pungent odours, as this usually indicates a potential food source for BSF offspring, or other biochemical signals derived from BSF eggs or gravid BSF females. BSF adults require specific environmental conditions to induce mating behaviors, including specific ranges of light, space, temperature and humidity. BSF will survive and mate at temperatures between 22° C. and 35° C. and humidity levels between 30% and 90%, and for example, BSF will survive and mate at an ambient air temperature of approximately 25° C.-30° C. with a relative humidity of approximately 60-80%. It has been reported that a BSF colony can be maintained at 22° C. (Tomberlin and Sheppard, 2002) and that the upper limit for optimal development of the BSF is between 30-36° C. (Tomberlin et al., 2009). A study measuring BSF mating and oviposition reported that 80% percent of egg clutches were deposited when humidity exceeded 60% (Tomberlin and Sheppard, 2002).

BSF larvae have been produced for a variety of purposes, including: treating organic liquids (US20120187041), and digesting solid organic waste for the purpose of waste management or production of livestock feed (U.S. Pat. No. 6,938,574, US20030233982, US20040089241, US20110296756, US20030143728, US20020177219), and therapeutics (U.S. Pat. No. 6,557,487). Similarly, fly larvae have been used in a variety of processes involving bioconversion of organic materials, such as processes described in U.S. Pat. No. 8,322,305 for making fertilizer from swine feces/urine using *Musca domestica*.

Wireworms, the larval stage of click beetles (order Coleoptera; family Elateridae) are pests of many agricultural crops, including: corn, sorghum, small grains, tobacco, sugar beets, beans, various vegetables, and potatoes. There are reportedly more than 9000 species of wireworm worldwide, and a number of these are currently recognized as serious agricultural pests, particularly of potato plants. For example approximately 30 species are recognised as pests in Canada, and a National Wireworm Species Distribution Map has been produced by Agriculture and Agri-Food Canada, identifying the distribution of more than 20 wireworm pest species in Canada, including: *Agriotes criddlei, A. lineatus, A. mancus, A. mellillus, A. obscurus, A. sputator, Aeolus mellillus, Athous* sp. *C. cylindriformis, C. destructor, C. lobata, C. morula, Ctenicera* sp. *H. abbreviatus, H. nocturnus, Hemicrepidius* sp., *L. agonus, L. californicus, L. canus, Limonius* sp. *M. communis,* and *Melanotus* sp.

SUMMARY

In various aspects, the invention provides methods for reducing or inhibiting Coleopteran insect pest damage to a crop susceptible to the Coleopteran insect pest, or for repelling or inhibiting the Coleopteran insect pest, or for increasing yield of a crop, comprising applying an effectifve amount of black soldier fly frass to the soil or to the crop. The frass may for example be applied by being worked into the soil before planting the crop, may be applied to the soil at least one week prior to planting the crop. Crops may for example include: corn, sorghum, small grain, tobacco, sugar beet, bean, vegetable, lettuce, bok choy, or potato. The frass may for example be applied at a rate of at least about 5 tonnes per Hectare, or 8% dry weight frass to dry weight frass plus soil, for example at a rate that kills at least 50% of the insect pest.

Methods of the invention may be used to treat a variety of wireworm pests, for example: *Agriotes criddlei, A. lineatus, A. mancus, A. mellillus, A. obscurus, A. sputator, Aeolus mellillus, Athous* sp. *C. cylindriformis, C. destructor, C. lobata, C. morula, Ctenicera* sp. *H. abbreviatus, H. nocturnus, Hemicrepidius* sp., *L. agonus, L. califomicus, L. canus, Limonius* sp. *M. communis,* or *Melanotus* sp.

The term "frass" is generally understood to refer to the excrement of insect larvae, or the refuse left behind by boring insects. In the context of the present invention, BSF frass connotes a mixture that includes excretia of BSF larvae, exuvia of larvae and other parts from other BSF stages of development (including dead eggs, larvae, pupae or adults), indigestible material, for example fibrous or cellulose based material, other metabolic products, for example, hormones, antibiotics or enzymes, chitin, and other organisms associated with this organic mixture, such as bacteria, fungi, protozoa and yeasts. In selected embodiments, BSF frass is the result of a process in which the majority (≥50%, up to 100%) of the dry matter of a feedstock passes through the digestive system of the BSF larvae, to produce residue that constitutes BSF frass.

In accordance with one aspect of the invention, BSF frass has been shown to have beneficial effects on plant growth and survival. In exemplary embodiments, BSF frass of the present invention contains macronutrients, for example characterized by having NPK at levels approximating 5-2-2. As such, BSF frass of the invention can be used as a fertilizer or soil additive, for example at an application rate appropriate for selected plant and soil characteristics.

In alternative aspects of the invention, BSF frass has been shown to have properties that confer protective effects against plant pathogens. In exemplary embodiments, BSF frass of the invention may accordingly be used for reducing or inhibiting pest damage to a susceptible crop. For example, to reduce or inhibit damage caused by wireworms.

Various embodiments of the invention provide methods for converting organic material. For example, such methods may include isolating BSF eggs using apparatus adapted for that purpose, distributing the BSF eggs in an environment containing organic material, and maintaining the BSF eggs in the environment until the BSF eggs hatch to become BSF larvae capable of converting organic material, for example converting the material to frass. The BSF eggs may be maintained in a vessel containing organic waste material.

BRIEF DESCRIPTION OF THE DRAWINGS

FIG. 3A is a perspective view of a pupation chamber utilizing a drawer system for use with various embodiments of the invention.

DETAILED DESCRIPTION

Various embodiments of the invention provide an apparatus and methods for producing and isolating BSF eggs in a self-contained environment, including the inducement of mating and the convenient isolation and collection of eggs with minimal disruption of fly behaviors. The following exemplary embodiments are provided for illustrative purposes, and are not intended to be limiting.

Figure 1:
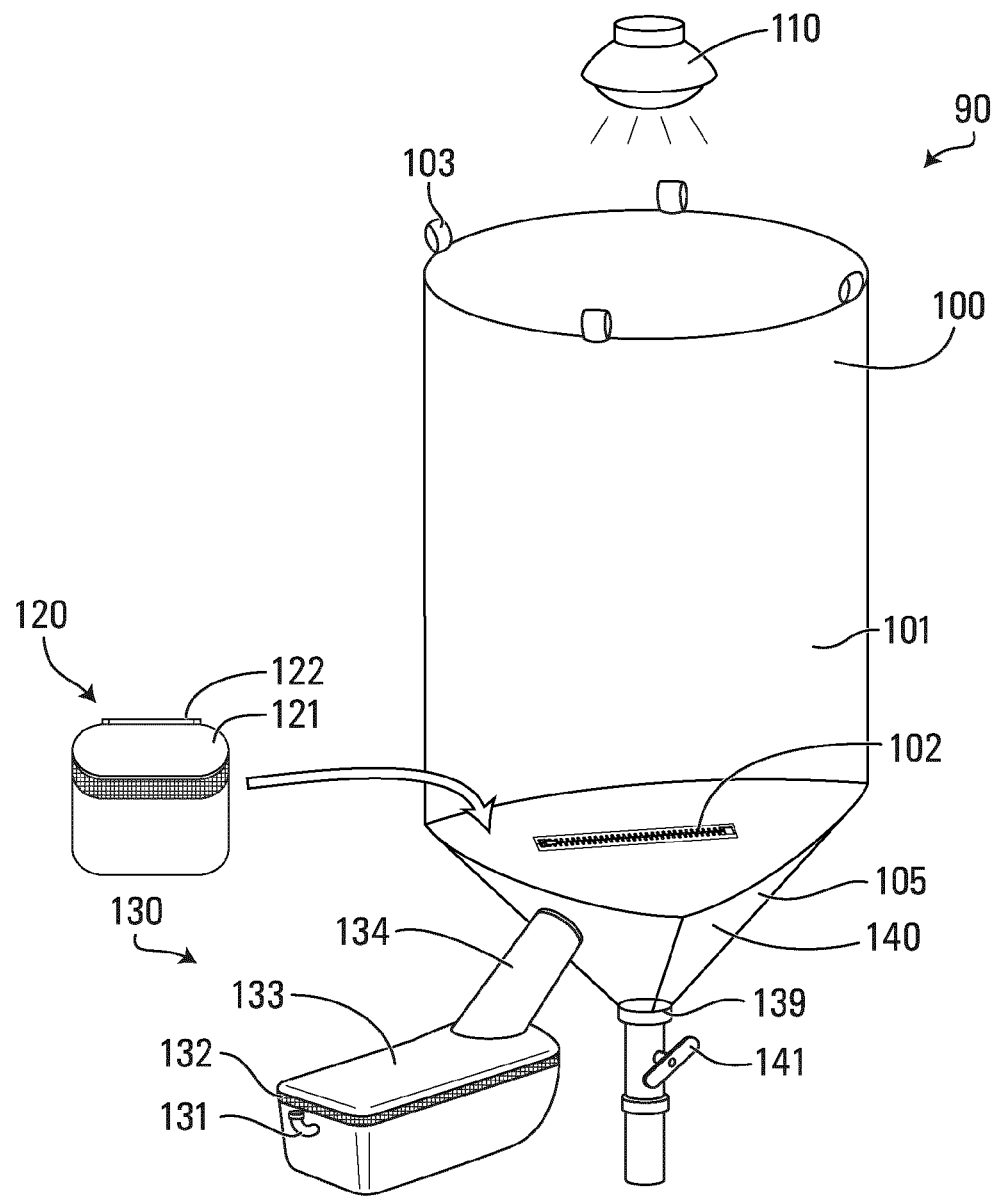
FIG. 1 is a perspective view of an apparatus for producing black soldier fly eggs according to a first embodiment of the invention.

Referring to FIG. 1, an apparatus for producing and isolating BSF eggs according to a first embodiment of the invention is shown generally at 90. The apparatus includes a mating chamber 100, an artificial light source 110, and an oviposition chamber 120 in communication with the mating chamber. Optional features include a pupation chamber 130 and a mort chamber 140, both of which can be placed in communication with mating chamber 100.

Mating Chamber.

Mating chamber 100 is defined by a plurality of walls, e.g. cylindrical upper wall 101 and lower conical wall 105. A person of ordinary skill in the art will understand, however, that mating chambers according to various embodiments of the invention may be defined by any number of walls, including a single wall. Walls 101 and 105 may be constructed from a plastic mesh material or other appropriate material. For example, walls 101 and 105 may be constructed of Lumite (Lumite Co., Baldwin, Ga.) because it is durable, heat- and UV-resistant. Further, light colored materials (e.g., white or yellow) may be used as they reflect light and may also encourage BSF mating. The mating chamber 100 may be of any reasonable size and shape, for example a square or cylinder. Preferably, the bottom of the mating chamber is conical or v-shaped. For example, the mating chamber 100 may be generally cylindrical with a total volume of approximately 1.3 m$^3$. Further, and for example, the height of the mating chamber 100 will be limited (for example, to approximately 3 m or less) based on light diffusion from above. Alternatively, the generally cylindrical upper wall 101 (e.g., ~1.5 m in height, ~0.9 m in diameter) may be connected at the bottom to wall 105 which defines a funnel-shaped mort chamber 140.

Wall 101 includes a means of accessing the chamber 100 from the exterior, e.g. zipper 102 (e.g., ~90 cm long) located approximately 15 cm from the top of the mort chamber 140. However, a variety of sealable openings may be used. Additional access points may be provided as needed. For example, an approximate 0.15 m opening in wall 101 may provide an additional access for pupation chamber 130. The top of wall 101 may include a plurality of loops 103 for suspending the mating chamber 100 off the floor. Additional loops may be included on the inside of the mating chamber 100 from which plastic mesh or other suitable material may be suspended to increase the inner surface area for adult BSF to rest on (not shown in Figures).

The mating chamber 100 may be maintained at an air temperature of approximately 29° C. with a relative humidity of approximately 70%. Humidity may be maintained with, for example, a manual or automated humidifier; for example, a Sunbeam® humidifier may be employed. While adult BSF do not eat, they may be kept hydrated using a hydration system. Serving as an example, an Exo Terra® Monsoon RS4000 High Pressure Rain System may be installed and programmed to spray distilled water for approximately 12-16 seconds at 1 hour intervals.

Adult BSF may be added directly to the mating chamber 100 through an opening, e.g., through the zipper 102. Alternatively, adult BSF may be added indirectly to the mating chamber 100 by adding pupae or prepupae to pupation chamber 130 through the pupation chamber portal 131. Pupation chamber 130 may be in communication with mating chamber 130 by means of conduit 134. Accordingly, newly emergent adult BSF may migrate from the pupation chamber 130 to tubular conduit 134, and toward mating chamber 100.

The pupation chamber 130 may be constructed from any appropriate material, for example plastic or metal, according to any reasonable dimensions. For example, a plastic tote of approximate dimensions 2×1.5×1.5 feet may be used. The pupation chamber 130 may be kept at approximately 60-95% humidity, for example 80-90% humidity. The pupation chamber 130 may be kept at approximately and 25° C.-35° C., for example 28° C.-30° C. using a control system and probe (e.g., Zoo Med's Hydrotherm™). For example, humidity may be introduced with a fogging system (serving as an e.g., Zoo Med's Repti Fogger™ Terrarium Humidifier) and heat may be applied with a standard electric heating cable or ceramic heater or any other suitable heater. Dehumidification may be applied with a blower system.

BSF pupae or prepupae may be introduced to the pupation chamber 130 through a pupation chamber portal 131, which for example may be a PVC tubular conduit with cap located on the upper side of the pupation chamber 130. The top of the pupation chamber 130 may be covered with a mesh screen 132 that tapers to a tubular conduit 134 connecting the pupation chamber 130 with the mating chamber 100 or mort chamber 140. In the illustrated embodiment, conduit 134 connects the pupation chamber 130 with the mort chamber 140, which in turn is in communication with the mating chamber 100. The conduit 134 may be made of mesh or any other suitable material. A cover 133 may be placed over the mesh screen 132 to keep humidity inside and light out. The cover 133 may be made of plastic or any other suitable material. The opening to the conduit 134 is not blocked by the cover 133 so that when adult BSF emerge from pupation they are attracted to light shining from above through a sidewall of the tubular conduit 134, or light shining through tubular conduit 134 from mating chamber 100. Adult BSF may fly or walk through tubular conduit 134.

The tubular conduit 134 may be angled at approximately 0 to 45 degrees relative to the base of the pupation chamber 130 to allow for light to enter, while maintaining an angle that matches the typical flight angle of BSF adults.

Referring to FIG. 3A, a pupation chamber according to various embodiments of the invention is shown generally at 330. Pupation chamber 330 includes a system of drawers 354 supported by a hollow frame 351. The system of drawers 354 allows for temporal (age) organization of the prepupae which enter chamber 330. The system further allows for easy removal of empty pupation exuviae after emergence has completed, and restocking of new prepupae. The system can provide drawer-specific control of environmental conditions (e.g., temperature and humidity). A yet further advantage of the drawer system is that it allows for expansion through the addition of additional drawer units into the system. Pupation chamber 330, for example, may be provided with eight (8) drawers, however a person skilled in the art will understand that only a subset of the total drawers may be used at any time.

Figure 3B:
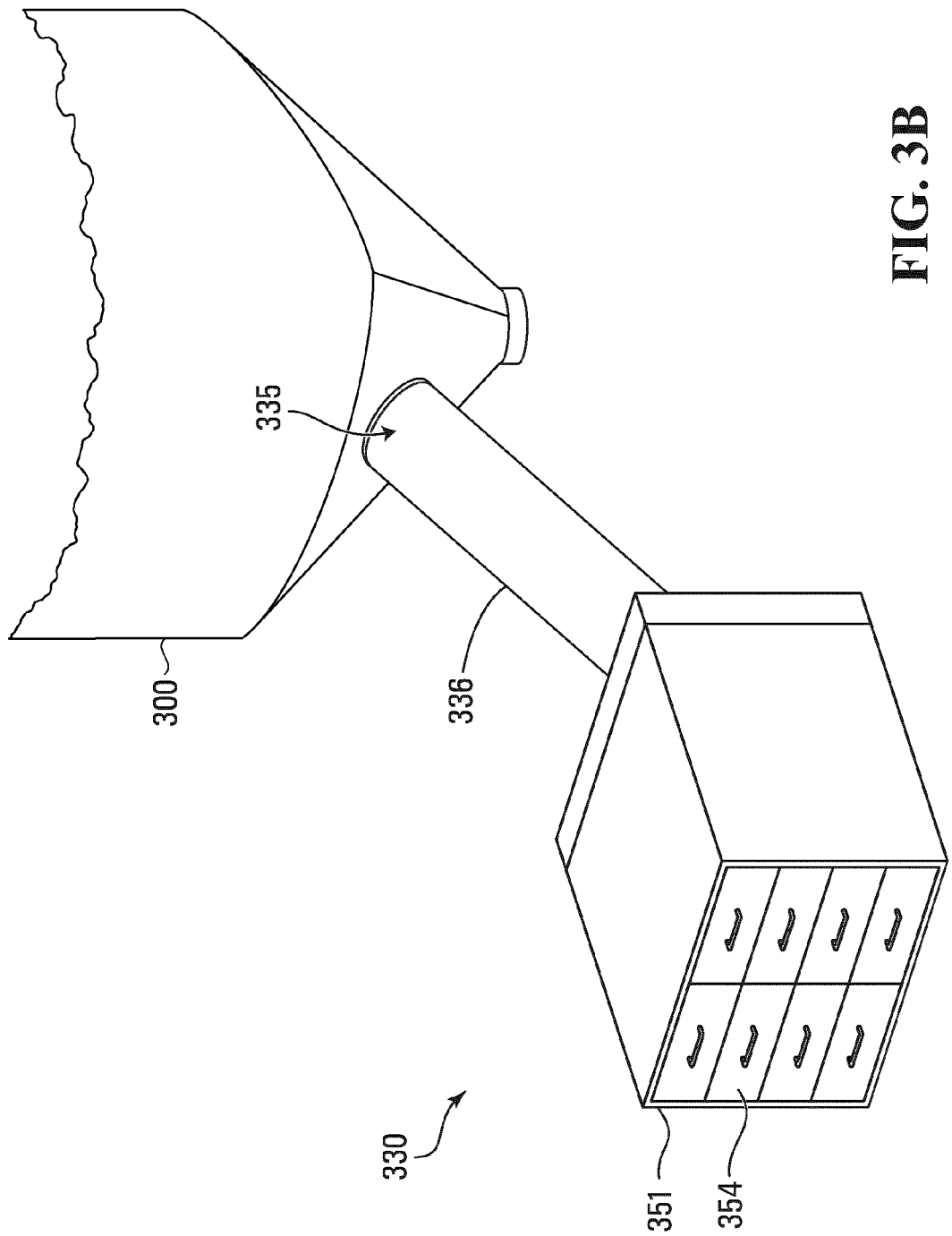
FIG. 3B is a perspective view of a pupation chamber utilizing a drawer system for use with various embodiments of the invention.

Referring still to FIG. 3A, pupation chamber 330 is connected from behind to the mating chamber 300 by tubular conduit 334. Tubular conduit 334 is made of a mesh material, however, a person skilled in the art will understand that it could be made of other materials, such as a non-mesh tube illustrated in FIG. 3B. Prepupae are loaded into each drawer 354 from the front end of the pupation chamber 330. A set of emergence holes (not shown) are positioned at the back of each drawer to provide an exit for the newly emerged adult BSF into conduit 334.

Adult BSFs are drawn to the exit holes at the back of the drawer due to illumination of conduit 334 by ambient light shining through the mesh, or the artificial light source of the mating chamber 300. Alternatively, an artificial lighting system external to mating chamber 300 can be employed to attract emerging adult BSFs from pupation chamber 330 into conduit 334. For example, LED lights can be provided on the interior of the conduit 334 to attract emerging adult BSFs. To assist in directing the movement of newly emerged adult BSFs, the pupation chamber 330 is enclosed within a dark fabric which only allows light to penetrate through exit holes at the back from conduit 334. Once in conduit 334, BSFs migrate through the conduit and into mating chamber 300 through opening 335 defined by a wall of the mating chamber.

Figure 4A:
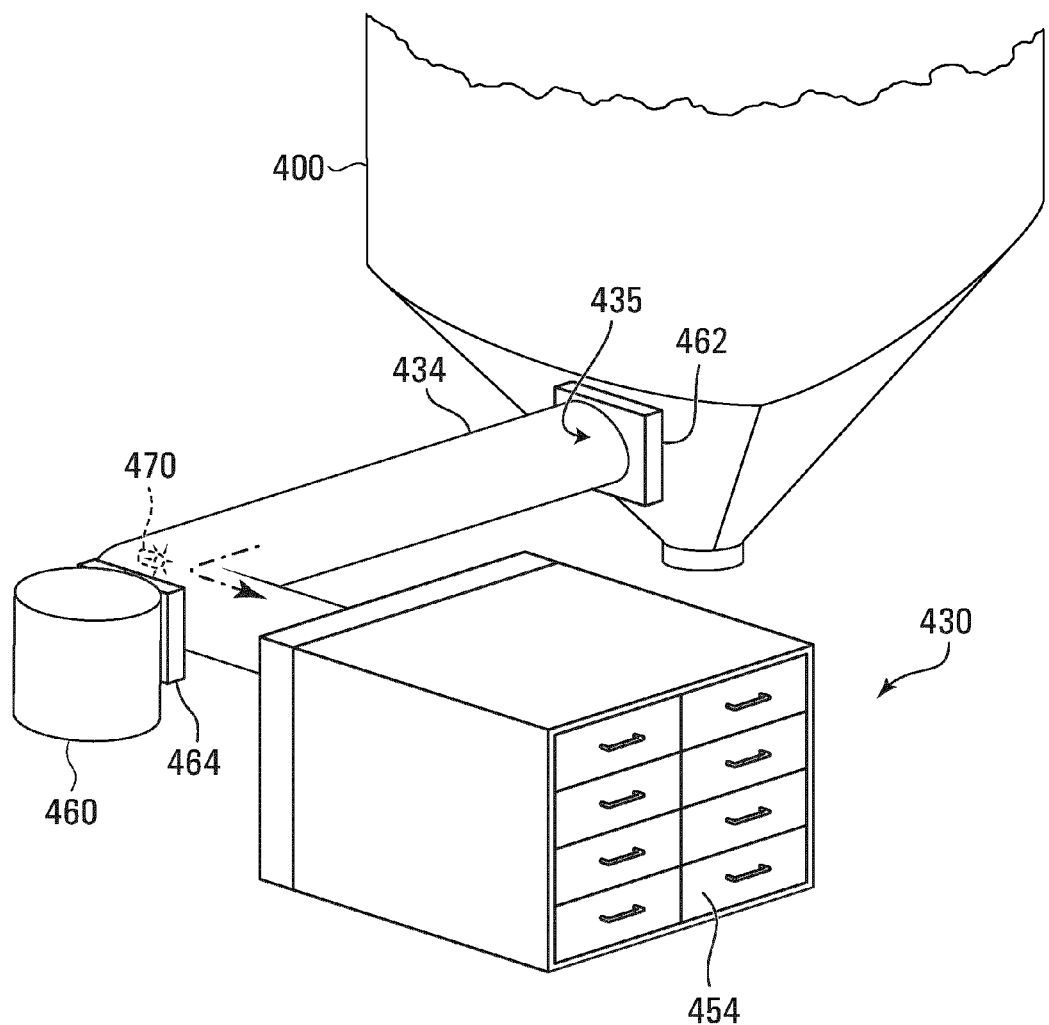
FIG. 4A is a perspective view of a pupation chamber utilizing a blower to blow emergent black soldier flies toward the mating chamber.
Figure 4B:
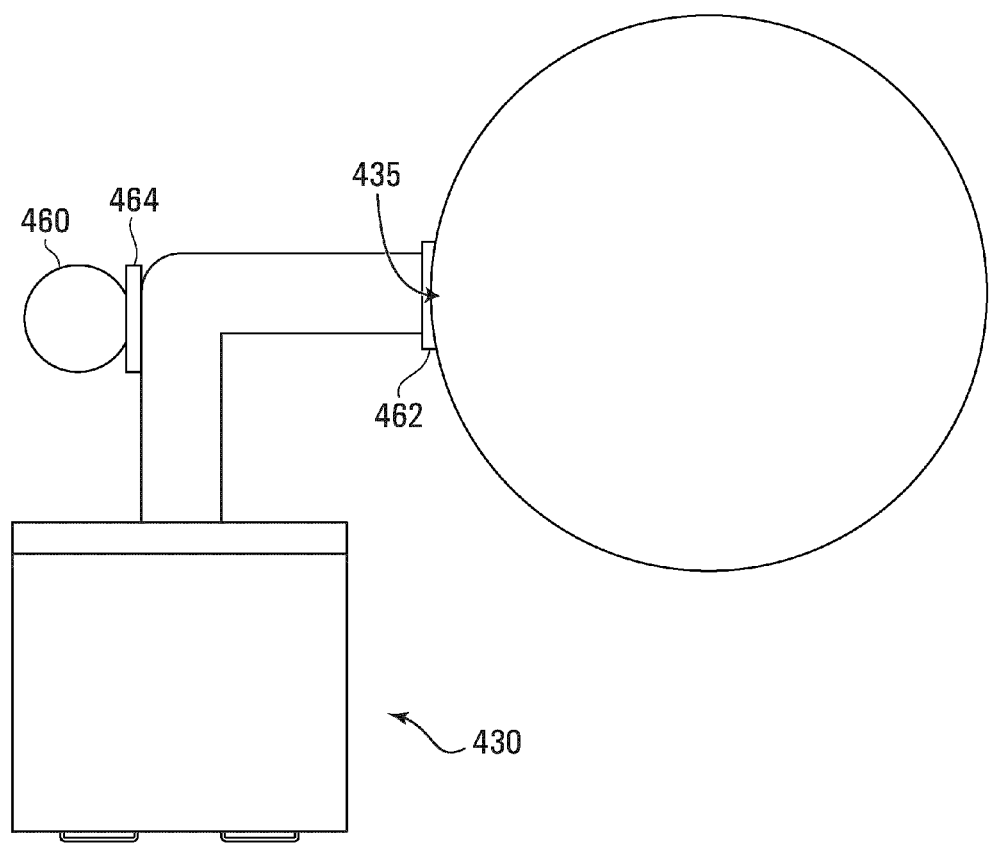
FIG. 4B is a top view of the pupation chamber illustrated in FIG. 4A.

Migration of newly emerged BSFs to the mating chamber does not have to be an entirely passive process as described above. FIG. 4 illustrates an embodiment of the invention in which a blower is used to blow BSFs in the conduit toward the mating chamber. In the illustrated embodiment, pupation chamber 430 is connected to mating chamber 400 by T-conduit 434. In the illustrated embodiment, T-conduit 434 is horizontal such that the entrance to the conduit from the emergence openings(s) of pupation chamber 430 is at the same height as mating chamber opening 435. However, a person skilled in the art will understand that conduit 434 need not be oriented horizontally, and that the entrance to the conduit and the maturation chamber opening 435 could be vertically offset from each other. Blower 460 is in communication with conduit 434, and configured to blow BSFs toward opening 435, and thus mating chamber 400. Attracted by light coming from conduit 434, newly emerged BSFs exit pupation chamber 430 into the conduit and are blown toward, and perhaps into, mating chamber 400. Blower 460 may be set on a timer to periodically blow, so as to allow for a plurality of BSFs to accumulate in the conduit 434 before they are blown toward the mating chamber 400. A check valve may used anywhere along the path between the blower 460 and the mating chamber 400 to prevent BSFs from retreating from the mating chamber to the conduit 434 or pupation chamber 430. In the illustrated embodiment, check valve 462 is positioned at opening 435. Check valve 464 opens due to pressure generated when blower 460 is in operation. Check valve 462 closes due to the decrease in pressure when blower 460 is off, which ensures that gravid female BSFs cannot retreat from the mating chamber 400 to oviposit eggs in the connector 434 or pupation chamber 430. Another check valve 464 may be positioned to seal blower 460 from conduit 434 to prevent flies from settling around or getting stuck in the blower. The conduit 434 may be shaped such that a venturi effect creates suction to aid the movement of flies from the pupation chamber 430 to the mating chamber 400. Blower 460 may also help ventilate the pupation chamber 430 and keep prepupae at the desired humidity and temperature. Alternatively, or in combination with blower 460, an artificial lighting system external to mating chamber 400 can be employed to attract emerging adult BSFs from pupation chamber 430 into conduit 434. For example, LED light 470 can be provided on the interior of the conduit 434 to attract emerging adult BSFs.

Figure 5:
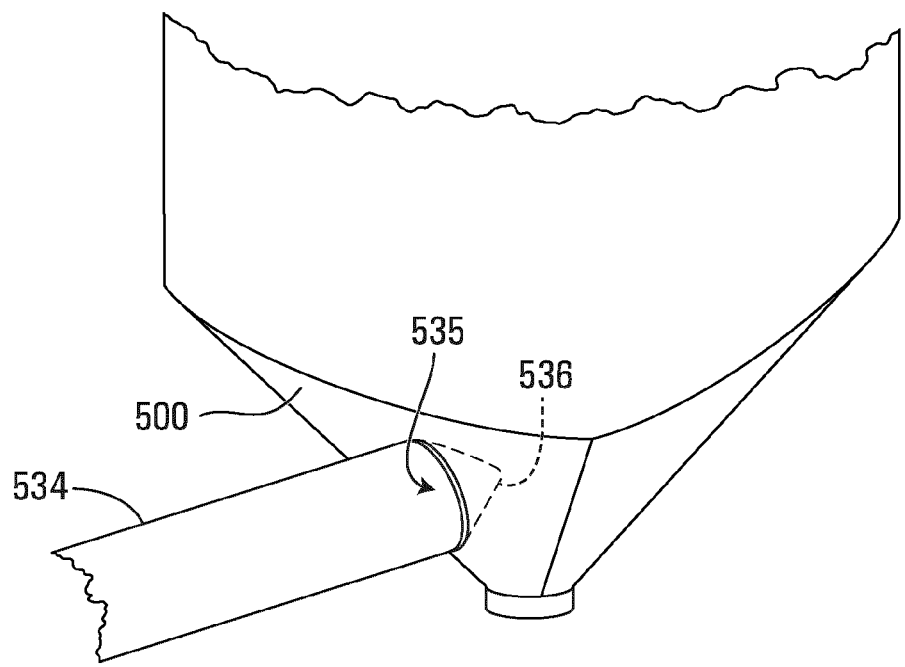
FIG. 5 is a perspective view of a connection between a pupation chamber and a mating chamber including a funnel trap for preventing retreat of black soldier flies from the mating chamber.
Figure 6:
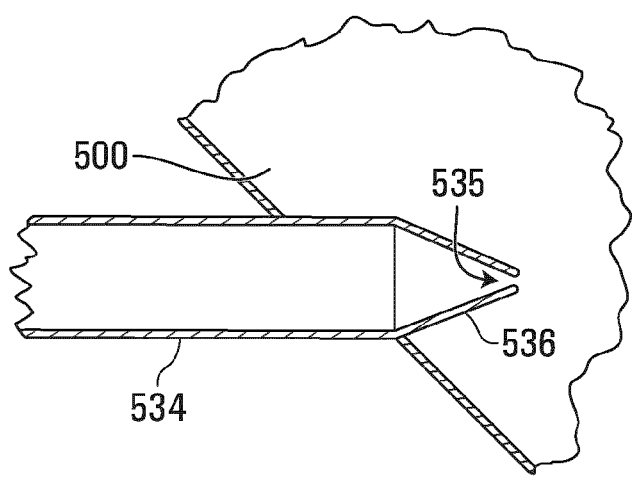
FIG. 6 a cross-sectional view of the connection illustrated in FIG. 5.

A person skilled in the art will further understand that alternative structures can be used, both with passive systems or systems employing blowers, to prevent retreat of BSFs from the mating chamber. FIGS. 5 to 8 illustrate the use of a one-way passage or duct to inhibit or prevent retreat of BSFs from the mating chamber 100. One-way passages will generally have a wide entrance and taper towards a exit of sufficient size and shape to permit passage of a BSF through, but sufficiently narrow and acute as to inhibit subsequent re-entry of the BSF into the one-way conduit. In one alternative, the one-way conduit includes a funnel, which may be generally frustoconical in shape (although other shapes may be contemplated). Referring to FIGS. 5 and 6, opening 535 to the mating chamber 700 is defined by funnel 536 which tapers toward the mating chamber 500. Accordingly, BSFs are funneled into chamber 700, and cannot retreat into conduit 534.

Figure 7:
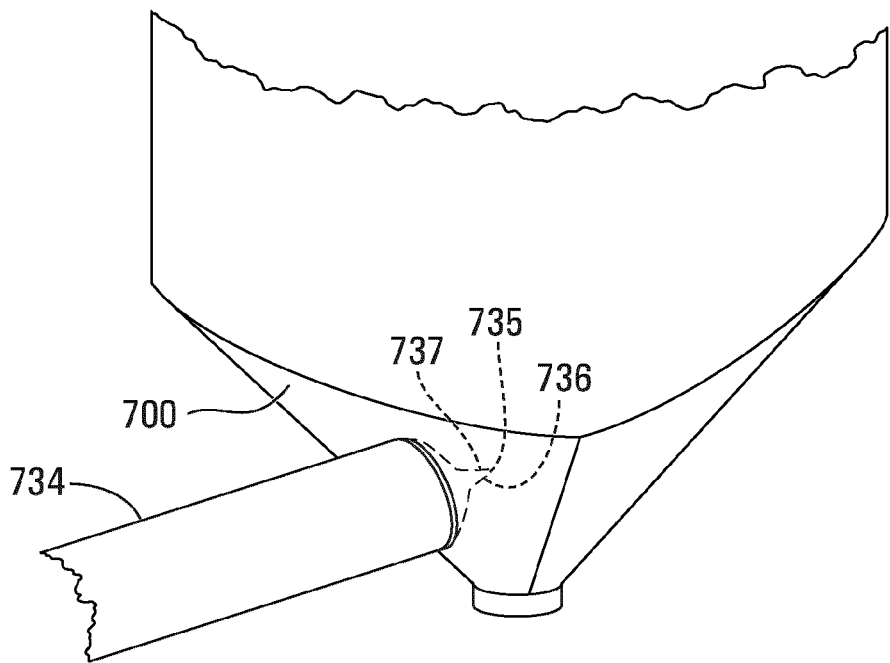
FIG. 7 is a perspective view of a connection between a pupation chamber and a mating chamber including a tapered slot with offset end edges for preventing retreat of black soldier flies from the mating chamber.
Figure 8:
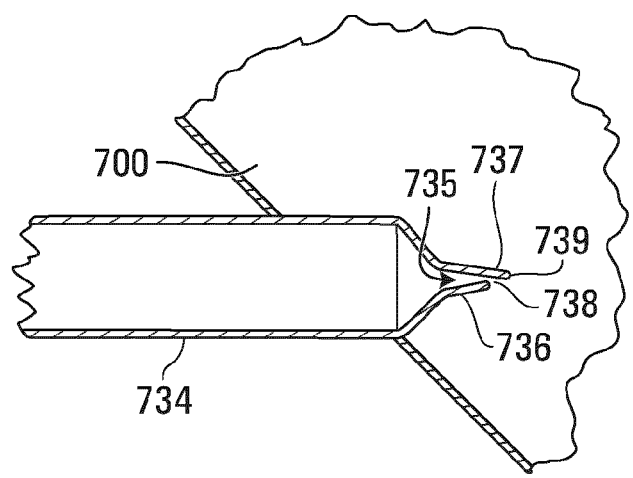
FIG. 8 a cross-sectional view of the connection illustrated in FIG. 7.

In another alternative illustrated in FIGS. 7 and 8, the one-way passage may be include a tapered slot comprising opposing walls 736 and 737 which taper toward each other from the entrance to the exit, i.e. slit 735. As seen in FIG. 8, edge portions 738 and 739 of walls 736 and 737, which define slit 735, are offset.

The illustrated one-way conduits may serve to prevent BSFs from retreating into the conduit for several reasons. A BSF may be unable to articulate its abdomen and thorax to an angle less than that required to make it through the hole 535 in FIG. 6 or slit 735 in FIG. 8. BSFs may be unable to fly directly into the hole 535 or slit 735 where the width of the wingspan approaches or is greater than the width of the hole or slit. Where the overlapping edge portion of slit 735 extends beyond the underlapping edge portion 738 by less than the length of a BSF, a BSF may be unable to easily land on the underside of the overlapping edge 739, and thus be discouraged from landing parallel to the slit 735.

While one-way conduits have been illustrated in association with the mating chamber opening, it will be appreciated that the one-way conduits could be positioned anywhere in the conduit between the pupation chamber and the mating chamber opening and still achieve a desired effect of preventing retreat of BSFs, especially gravid BSFs, toward the pupation chamber.

Furthermore, while the illustrated embodiments show the use of conduits to connect mating chambers with external pupation chambers, a person skilled in the art will understand that it is sufficient that the pupation chamber and the mating chamber are in communication with each other. Accordingly, in a simplified embodiment of the invention, the pupation chamber may be positioned directly within the mating chamber. BSF pupae or prepupae may be introduced to the pupation chamber outside the mating chamber. Once the BSF pupae or prepupae are introduced into the pupation chamber, the pupation chamber can be placed within the mating chamber. Provided that the pupation chamber remains in communication with the mating chamber, e.g. by way of an emergence hole(s) in the walls or ceiling that define the pupation chamber, and that light from the mating chamber can penetrate into the pupation chamber to attract newly emerged BSFs adult from the pupation chamber to the mating chamber, a further conduit to connect the pupation chamber and mating chamber is not necessary. Nevertheless, one way passages or ducts may be used in combination with emergence holes to prevent BSF adults from re-entering the pupation chamber from the mating chamber.

Figure 2:
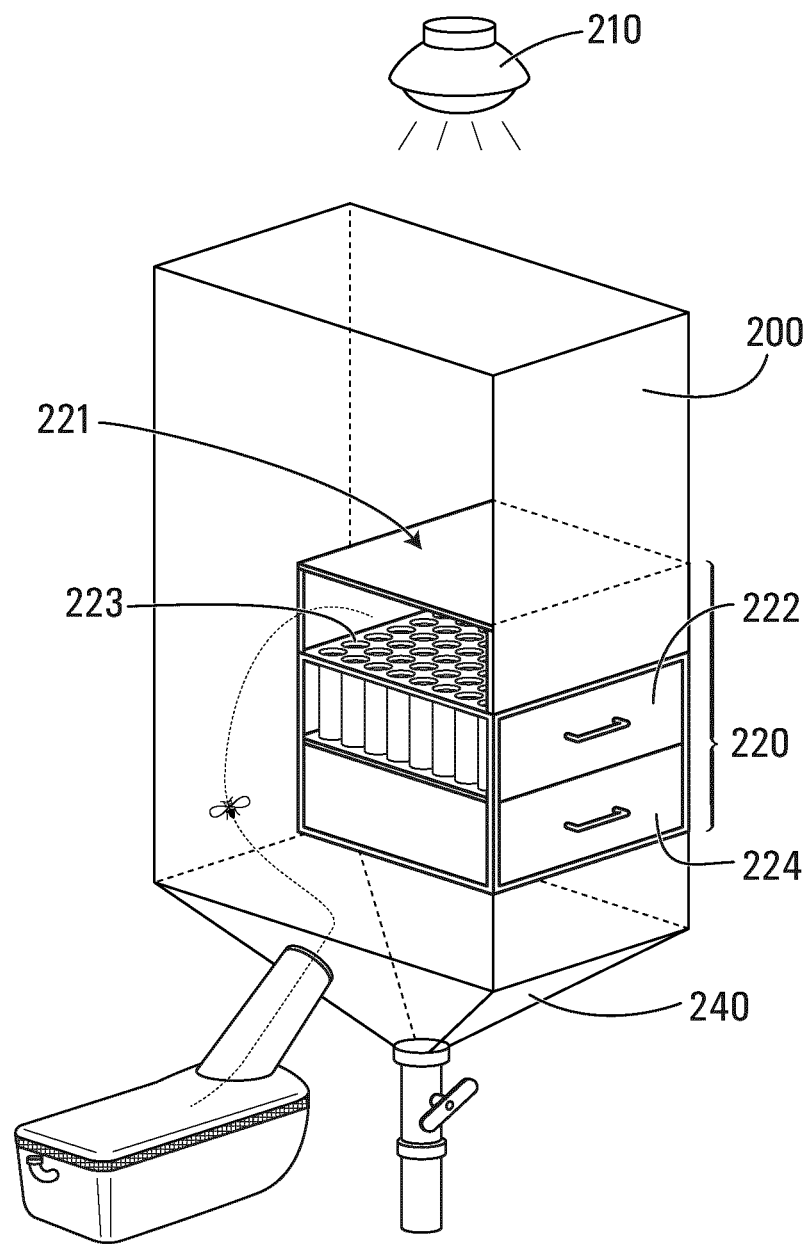
FIG. 2 is a perspective view of an apparatus for producing black soldier fly eggs according to a second embodiment of the invention in which the oviposition chamber is accessible from outside the apparatus using a drawer system.
Figure 9:
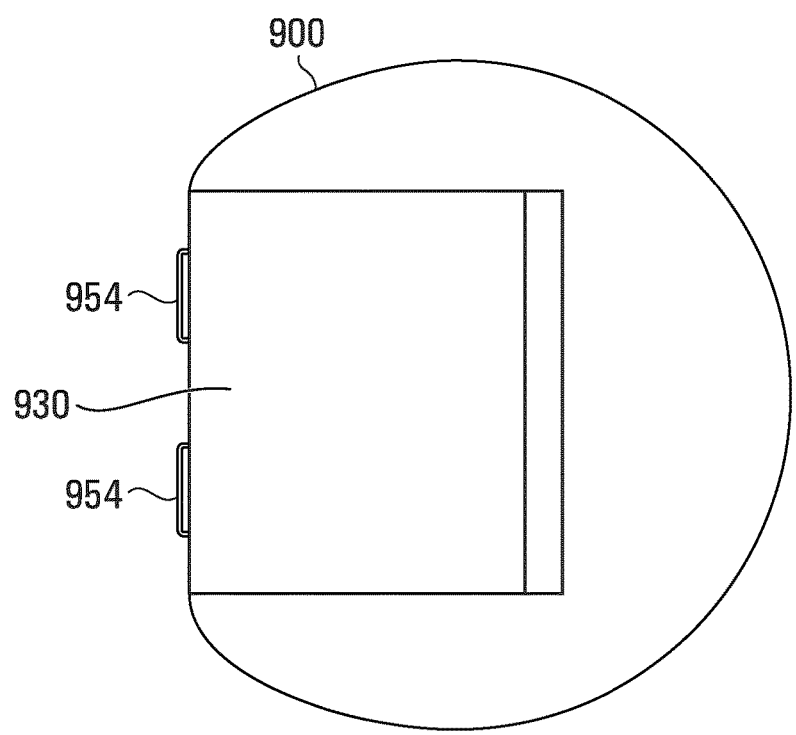
FIG. 9 is a cross-sectional top view of an embodiment of the invention in which the pupation chamber is positioned within the mating chamber and comprises a drawer system by which pupae and prepupae may be intoducted to the pupation chamber from the exterior of the mating chamber.

As a further alternative design for a pupation chamber, and referring to FIG. 9, mating chamber opening of mating chamber 900 may be designed to accommodate drawers 954 of pupation chamber 930, such that the pupation chamber may be positioned within the mating chamber yet the contents of the drawers may be accessed from the exterior of the mating chamber. Such design, which may be similar to that discussed below for the oviposition chamber as illustrated in FIG. 2, facilitates the introduction of the pupae and prepupae to the system without entering the mating chamber 900 or allowing adult BSF to escape. The pupation chamber 930 may be sewn into the mating chamber and supported from the mating chamber frame structure or supported from above by rope, chain or rods, or other suitable means.

Referring again to FIG. 3, the capacity of prepupae for each drawer 354 of the drawer system is dependent on the desired population size for the mating chamber 300. A rotating pupae input system (based on the development time required for prepupae to mature into adults) can be utilized to sequence the availability of empty drawers as desired. Further, individual environmental temperature control devices may be installed into each drawer 354 for controlling environmental conditions therein.

Mort Chamber.

Referring again to FIG. 1, once in the mating chamber 100, adult BSF live approximately 7 to 10 days. On about day 2-4, females mate with males. On about days 3-5 they lay eggs. Around day 7 to 10, BSF die and collect in the funnel-shaped mort chamber 140 at the bottom of the mating chamber 100. At the bottom of the mort chamber 140 is an opening 139 (for e.g., 0.15 m in diameter) fitted with a manual or automated valve 141, which facilitates the daily or periodic collection of mortalities. Alternatively, if the mort chamber is v-shaped such that the mortality chamber is a long trough, a trough cleaning mechanism may be used to sweep mortalities to one end of the trough for collection through a gate or valve.

Artificial Light Source. Referring still to FIG. 1, an artificial light source 110 is shown suspended above the mating chamber 100. There may be more than one artificial light source. For example, the light source 110 may be placed approximately 0.15 m above the top of the mating chamber 100. For example, a 500 W quartz-iodine light source (Model QVF135, Philips Lighting Ltd.) is reported to provide a spectrum between 350-2500 nm at 135 $\mu mol \cdot m^{-}$ 2·s⁻¹ light intensity. This light reportedly achieved 61.9% BSF mating success relative to natural sunlight under conditions of 28-30° C., 60-90% humidity, and access to drinking water via a spray every 2-3 hours (Zhang et al., 2010). Reproducing these same conditions in-house achieved 51% mating success (see Example 1, Table 2 herein). As described below, it was discovered that the addition of a halogen light source (e.g., a 50 W Exo Terra® Sunglo Halogen bulb or 50 W Halogen Neodymium Daylight bulb), which produces low intensity UBA and UVB, visible, and infrared wavelengths to the quartz-iodine light source improved mating success. The highest degree of mating success was observed when a 300 W quartz-iodine light was used in combination with a 50 W halogen light (see: Example 1, Table 2 herein). Light fixtures were placed approximately 30 cm from their center points and angled toward each other at an angle of 15 degrees such that the wavelengths from the emitted light sources overlap. In another embodiment, natural sunlight may be used as a supplemental light source and/or a single light source may be used that emits a broader range of wavelengths than the combination described above, but is modified with filters to provide substantially the same intensities and wavelengths as the combination of the quartz-iodine and halogen light sources. A light and darkness cycle may be used to emulate day and night. Serving as a non-limiting example, the total light source (both bulbs) may be turned on for a light period of 9 hours from 0800 h to 1700 h, and turned off for a darkness period of 15 hours from 1701 h-0759 h.

Oviposition Chamber.

Referring still to FIG. 1, the oviposition chamber 120 may be placed inside the mating chamber 100; for example, the oviposition chamber 120 may be supported by a rack (not shown in FIG. 1) affixed to the walls of the mating chamber 100 or it may be supported from the bottom or top of the mating chamber 100. Alternatively, the oviposition chamber 120 may be separate but connected to the mating chamber 100, so long as the mating chamber and oviposition chamber are in communication. FIG. 1 shows an example of an oviposition chamber 120 constructed of a plastic bucket, with a lid 121. Serving as a non-limiting example, the oviposition chamber lid 121 is propped open from the lid hinge 122 with a wire stopper. This creates an entrance and exit to the oviposition chamber 120, and also creates a dark environment which promotes ovipositing by the female BSF. Egg laying materials are placed on the inner walls of the bucket. For example, the egg laying materials may be blocks of corrugated cardboard; female BSF will oviposit eggs into the openings of individual "flutes" in the cardboard. Serving as a non-limiting example, the dimensions of flute openings may be approximately 3 mm×3 mm. Further, and for example, cardboard blocks may be constructed from stacks of three strips of approximately 3×10 cm cardboard held together with tape, but leaving the flute openings uncovered. Further, egg laying material may be plastic or metal with equivalent sized holes ranging in size from 2-4 mm in diameter. The shape of the hole openings may be circular, elliptical, half circles, square or variations thereof. An attractant is placed in the bottom of the bucket to draw gravid (i.e., pregnant) female BSF to the oviposition chamber 120. An example of an attractant is a saturated 1:1 mixture of Gainesville diet (Hogsette, 1985) mixed with BSF larvae leachate and BSF castings. Other attractants can include fermenting grain, such as corn brewery grain, manure, decomposing food waste, BSF larvae and/or eggs. Any or all of these in various combinations will attract gravid female BSFs.

Referring to FIG. 2 now, an alternative design for an oviposition chamber is shown generally at 220. As alluded to above, wall 201 of mating chamber 200 defines an additional opening for accommodating drawers 222 and 224 of oviposition chamber 220, such that the oviposition chamber may be positioned within the mating chamber yet the contents of the drawers may be accessed from the exterior of the mating chamber. This design facilitates the collection of BSF eggs without entering the mating chamber 200 or allowing adult BSF to escape.

The oviposition chamber 220 may be sewn into the mating chamber 200 and supported by a cross piece (not shown in FIG. 2) from the mating chamber 200 frame structure or supported from above by rope, chain or rods, or other suitable means. Serving as a non-limiting example, the oviposition chamber 220 may be sewn into the mating chamber 200 at a height of approximately ⅓ of the total mating chamber 200 height from the mort chamber 240. Gravid female BSFs prefer to oviposit out of direct light; accordingly, a floating roof 221 may be used to provide shade from the artificial light source 210 and keep egg laying material dry and away from the mist. The top drawer 222 may contain egg-laying materials 223 consisting of, for example, vertically-oriented plastic or cardboard flutes or tubes that are open at both ends (as detailed herein). The bottom section of the top drawer may be perforated to allow for the scent of attractant to diffuse from the bottom drawer into the top drawer 224. A sweeper (not shown in FIG. 2) may be fixed to the frame of the oviposition chamber 220 to gently remove any adults that may be laying eggs or resting on the egg laying material as the drawer is opened. The bottom drawer may contain a saturated 1:1 mixture of Gainesville diet mixed with BSF larvae leachate and BSF castings, or other suitable attractants (as detailed herein), to draw gravid female BSFs to the egg laying materials 223 above it. A metal sheet (not shown in FIG. 2) may be used to slide between the top and bottom drawers (222 and 224, respectively) to cover the bottom drawer 224, when the top drawer 222 is removed for egg collection or when the attractant is being replaced to prevent undesired adults accessing and/or landing in the attractant. Alternatively, a single drawer may be used whereby the vertically oriented tubes are held above the attractant with tabs, such that the top of the tubes are flush, i.e. lay in substantially a common plane, with the top of the drawer. Drawers 222 and 224 are located tight to the frame to discourage females from laying eggs in crevices and the frame is enclosed on the sides and bottom to prevent adults escaping when drawers are opened.

The egg laying materials 223 containing eggs may be collected within approximately 0-24 hours after the eggs have been laid.

In a scaled up system, a long or rectangular cage for example, up to 100 feet long and less than 6 feet wide can contain open or closed containers (prepupae chambers) on a rail system, such that a series of prepupae chambers enter an inlet at one end of the cage and transition to the other end of the cage, where they exit the cage through an outlet or transition to another rail system that returns them to the an outlet at their origin. Each prepupae chamber will have a residency time in the cage for a period of time that allows >75% of the prepupae metamorphose into adult flies, for example 24 days. Prepupae chambers exiting from the cage arecleaned and restocked. Similarly, empty ovipositioning chambers would enter one end of the cage onto a rail system and they would be retrievable either at the same end of the cage, or the opposite end every day or every second day. Multiple lights would be positioned above the cage, for example every 4 ft. The bottom ½ to ⅓ of the cage is v-shaped when viewed longitudinally, and funnels adult mortalities to a trough where they can be collected with a vacuum, flushed out with water or dumped using a trap door.

The apparatus(es) and methods detailed herein can be used in a more expansive "lifecycle" of the BSF. For example, BSF eggs generated using the apparatus(es) and methods detailed herein can be introduced to a digester that contains organic waste materials (for example, fruits, vegetables and fish offal). The BSF life cycle can proceed with the BSF larvae converting organic waste which is present in the digester. The life cycle can further proceed with BSF larvae becoming prepupae. Prepupae or larvae can be processed for further purposes (for e.g., livestock (aquatic or terrestrial), pet feed, or even foodstuffs for human consumption). Further, prepupae can be introduced into a self-contained hatchery apparatus (as described herein) for generating BSF eggs. Accordingly, it will be appreciated that a digester which supports organic waste materials can be used in association with the apparatus(es) and methods detailed herein.

Example 1: BSF Frass Production

In accordance with this aspect of the invention, BSF frass is produced by feeding BSF larvae at a selected density (larvae/unit volume or surface area), quantity of feed, frequency of feeding, and duration of feeding, under selected environmental conditions, with an appropriate evaporation rate, to achieve a final dry product, for example that is less than 30% moisture. Target moisture contents of the BSF Frass can for example be achieved during the process through active evaporation by blowing warm, dry air through or over the feeding surface, or after harvesting through passive or active drying techniques.

In exemplary embodiments, BSF frass production can be achieved using the following feeding protocol:

Larvae are fed in an environment having a temperature of 20-35° C., such as 25-35° C. and a relative humidity of 40-80%.

Larvae are fed an organic feedstock, which may be in varying stages of degradation, including, but not limited to: pre-consumer or post-consumer food waste (e.g. expired or past due packaged food, produce, deli waste, bakery waste), food processing by-products (e.g. brewery grains, produce, fish trimmings) and/or livestock manure.

Larvae are fed a feedstock having a selected average particle size that larvae can consume within 24 hours, for example less than about 1 inch in diameter, or in the alternative less than about ½ inch in diameter. If the average particle size is too large, larvae will only partially ingest the food, reducing the quality of the final product. Moreover, large particles will result in large fibrous particles, which will make the seiving-out of larvae less effective as there will be waste particle sizes larger than the length of a larvae.

Feed is applied to the surface of the larvae/frass and spread over the the surface of the material (larvae/frass). Feed is not mixed into the larvae/frass as this creates clumping of material and can result in larvae mortality. The material may be mechanically mixed or turned toward the end of the feeding process when material is dry enough such that clumping of material does not occur, for example, during the last ⅓ of the feeding time for example, days 14-21 in a 21 day growth cycle, in order to aid in the evaporation of water.

Larvae are produced from eggs that can be gathered from wild or domestic populations of adult flies, for example produced using the systems described herein. Larvae may for example be hatched within about 20 cm, or 15 cm, or 10 cm or 5 cm above an incubation feed, which can for example include any combination of the previously characterized organic feedstocks. A selected number of larvae may be fed in batches to achieve a uniform size of larvae, for example larvae collected within a 5 day period.

The number of larvae in each batch may for example be determined by: 1) dividing the total weight of eggs added to the batch by the average egg weight or 2) within 1 week following the incubation step, a sub-sample(s) of the batch is collected and the following data determined: number of larvae in the sample, the total weight of the subsample, and the total weight of the batch. The number of larvae=(# larvae/weight of subsample)×total weight of the batch.

Larvae may for example be fed a cumulative total of 0.1-0.3 g dry matter per larva over the 14-28 day period. The dry matter in the food may be determined by weighing a subsample of wet feed and dried to a constant weight using an oven or a moisture analyzer. Percent Dry matter of feed=(weight of dry feed/weight of wet feed)×100.

Larvae may be fed daily to maximize the surface feeding area over time and to calibrate the amount of feed depending on the developmental stage of the larvae. If too much feed is introduced early in the growth cycle, larvae will become trapped and will die. For example, incubation takes approx. 8 days, in which <5% of the total dry feed is fed to the larvae. On day 9, the larvae are transferred to a larger container containing 17-22% of the total dry feed. Larvae are then fed the following percentages of the total dry food on each day: 0% (Day 9), 0% (Day10), 9% (Day11), 9% (Day12), 9% (Day13), 9% (Day14), 9% (Day15), 9% (Day16), 9% (Day17), 9% (Day18), 5% (Day19), 5% (Day 20), 5% (Day 21).

Larvae may be reared over a period of 14-28 days, from egg hatching to harvesting Larvae may be maintained in relatively high densities of 10-25 larva/cm2.

The depth of material in each batch may be no more than that which allows larvae to access the bottom of the container, for example 4-6 inches. This aspect of the process may for example be carried out so as to maximize the probability of feed going through the digestive system of a larva at least once and to allow for adequate aeration of feed/digestate through the bioturbation activity of larvae.

Larvae may be either be allowed to crawl out of the BSF frass, and/or separated by density and/or size, for example, mechanically separated through sieving, screening and/or air clarification from the BSF frass.

Fractions that arise from the separation methods of the invention may for example include: BSF larvae, BSF middlings, and BSF frass. BSF larvae may include mature larvae, for example between 0.15 and 0.30 grams in mass. BSF middlings may include a mixture of larvae, large particle size frass, and other fibre or undigestible material. BSF frass may include, excretia of BSF larvae, exuvia of larvae and other parts from other BSF stages of development (i.e. dead eggs, larvae, pupae or adults), indigestible material, for example fibrous or cellulose based material or seeds; other metabolic products, for example, hormones, antibiotics or enzymes, chitin and organisms, for example bacteria, fungi, protozoa and yeasts associated with the above.

If seeds are present in the feedstock inputs, the BSF frass may be heated so as to render such seeds non-viable (ie. unable to germinate), for example to at least 64 C for 3.5 hours. Alternatively, the frass can be pulverized thus physically damaging the seeds. Failure to adequately render seeds in the frass inviable will result in an unsalable fertilizer.

Example 2: Field Effectiveness of BSF Frass Against Wireworm

Insecticidal BSF frass was produced by feeding larvae a mixture of food waste composed of approximately 70% produce, 20% breads or grains, 10% fish offal. A wide range of alternative feedstocks may be used in alternative embodiments.

In various aspects, the present invention is based on the observation that BSF frass exhibited pest control attributes, as an insecticide or insect repellant, as evidenced by the fact that other species of insects were not found to inhabit digestate of BSF larvae under selected laboratory conditions, in circumstance where other insects were provided access to the digestate. Field plots to demonstrate this activity were accordingly established at a site known to harbour *Agriotes lineatus* wireworms (in a geographic region known to harbour *Agriotes lineatus, A. obscures* and *Limonius canus*). Twelve plots were marked off within each of four blocks, with each block assigned to a different crop. Four replicates of each of three levels of frass (0 (control), 5 and 10 tonnes/Ha equivalents) were randomly assigned to plots within each block. Immediately after application of the frass, about the top 15 cm of soil on all plots (including the controls) were worked with a rake or pitchfork. All plots were then covered with burlap material. After two weeks, the burlap was removed and the soil surface was again worked. Two of the blocks were planted with starter seedlings: lettuce and bok choy. After approximately several days, the lettuce and bok choy plants on the control plots (0 tonnes/Ha frass) were in severe distress, consistent with wireworm feeding damage, while those on the frass-treated plots remained visually healthy and vigorous. Over the course of the next several days, the condition of the control plants worsened, consistent with ongoing wireworm feeding damage, resulting in eventual mortality greater than 90%, whereas the frass-treated plants continued to grow normally, with low mortality. Analysis of these results and the field conditions indicated that the BSF frass treatment exerted a protective effect against wireworm feeding damage, to which the plants would otherwise be susceptible.

Example 3: Insecticidal Frass Bioassays

In controlled bioassays, three species of wireworms were readily killed by the insecticidal BSF frass mixed with soil: *A. lineatus, A. obscurus* and *L. canus*. For example, in exemplary assays, eight percent frass in soil (dry weight frass/dry weight frass plus soil) killed 90-100% *A. lineatus* within 1-6 days, with lower concentrations killing a smaller proportion. For example, alternative batches of frass applied at a rate of 7.5% (dwt/dwt) killed from 28% to 88% *A. lineatus* in under five days. In general, 8% (dwt/dwt) frass reliably killed a high percentage of wireworms within 4 days. Similarly, 10% frass (dwt/dwt) killed 100% and 80% respectively of *A. obscurus* and *L. canus* after 24 hours. Frass also exhibited insecticidal activity against European chafer (Scarabidae), in assays evidencing 20% more chafer larvae killed after 20 days of exposure to 8% frass (dwt/dwt), compared to controls. Similarly, assays evidenced the effectiveness of BSF frass against cabbage root maggots, with frass killing larval and pupal stages, and reducing fly emergence.

Frass particles vary in size, and insecticidal activity may vary with the size of frass particles that are applied. In some assays, large frass particles that are reduced to fine particles are more toxic to wireworms than small particles reduced to finer particles. Alternative embodiments of the invention may accordingly involve grinding or sieving frass to obtain an insecticidal frass product having a desired particle size.

Field application of frass repelled adult click beetles, while wireworms were observed to consume frass. Accordingly, in some aspects, the invention involves using an insect trap comprising black soldier fly frass, so that the insect pest may be exposed to the BSF frass in the trap.

REFERENCES

1. Bradley, S. W. and Sheppard, D. C. 1984. House Fly Oviposition Inhibition by Larvae of *Hermetia illucens*, the Black Soldier Fly. *Journal of Chemical Ecology*, 19, 853.
2. Erickson, M. C., M. Islam, C. Sheppard, J. Liao, and M. P. Doyle. 2004. Reduction of *Eschericia coli* 0157:H7 and *Salmonella enterica* serovar *Enteritidis* in chicken manure by larvae of the black soldier fly. J. Food Protection. 67: 685-690.
3. Furman, D. P., R. D. Young, and E. P. Catts. 1959. *Hermetia illucens* (Linnaeus) as a factor in the natural control of *Musca domestica* Linnaeus. J. Econ. Entomol. 52: 917-921.
4. Hogsette, J. A. 1985. New diets for production of house flies and stable flies (Diptera: Muscidae) in the laboratory. J. Econ. Entomol. 85: 2291-2294.
5. Kabaluk, T., Janmaat, A, Sheedy, C., Goettel, M., and Noronha, C. 2013. *Agriotes* spp. L., Wireworms and Click Beetles (Coleoptera: Elateridae). In: Mason, P. and Gillespie, D. (eds) Biological Control Programmes in Canada. CABI, UK, 72-82.
6. Liu, Q., Tomerblin, J. K., Brady, J. A., Sanford, M. R., and Yu, Z. 2008. Black Soldier Fly (Diptera: Stratiomyidae) Larvae Reduce *Escherichia coli* in Dairy Manure. *Environ. Entomol.* 37(6): 1525-1530.
7. Sheppard, D. C J. K.; J. K. Tomberlin, J. A. Joyce, B. C. Kiser & S. M. Sumner. 2002. Rearing Methods for the Black Soldier Fly (Diptera: Stratiomyidae). *J. Med. Entomol.* 39(4): 695-698.
8. Tomberlin, J. K., Alder, P. H., and Myers H. M. 2009. Development of the Black Soldier Fly (Diptera: Stratiomyidae) in Relation to Temperature. *Environ. Entomol.* 38: 930-934.
9. Tomberlin, J. K. & D. C. Sheppard. 2002. Factors Influencing Mating and Oviposition of Black Soldier Flies (Diptera: Stratiomyidae) in a Colony. *J. Entomol. Sci.* 37(4): 345-352.
10. Tomberlin, J. K., D. C. Sheppard & J. A. Joyce. 2002. Selected Life-History Traits of Black Soldier Flies (Diptera: Stratiomyidae) Reared on Three Artificial Diets. *Ann. Entomol. Soc. Am.* 95(3): 379-386
11. Zhang, et al. 2010. An artificial light source influences mating and oviposition of black soldier flies, *Hermetia illucens*. J. Insect Sci. 10:1-7.

The invention claimed is:

1. A method for reducing or inhibiting Coleopteran insect pest damage to a crop susceptible to the Coleopteran insect pest, comprising applying at a site known to harbor wireworms an effective amount of black soldier fly frass to soil or to the crop to reduce or inhibit damage caused by wireworms, or exposing the Coleopteran insect to the black soldier fly frass, wherein the Coleopteran insect pest is a larva, prepupa or adult of a Click Beetle (family Elateridae).

2. The method of claim 1, wherein the method comprises repelling or inhibiting the Coleopteran insect pest in the soil or the crop by exposing the Coleopteran insect pest to the black soldier fly frass.

3. The method of claim 1, wherein the amount is effective for increasing yield of the crop grown.

4. The method of claim 1, wherein the wireworm is a: *Agriotes criddlei, Agriotes lineatus, Agriotes mancus, Agriotes mellitus, Agriotes obscurus, Agriotes sputator, Aeolus mellillus, Athous* sp., *Ctenicera cylindriformis, Ctenicera destructor, Ctenicera lobata, Ctenicera morula, Ctenicera Hemicrepidius abbreviatus, Hemicrepidius nocturnus, Hemicrepidius* sp., *Limonius agonus, Limonius californicus, Limonius canus, Limonius Melanotus communis*, or *Melanotus* sp.

5. The method of claim 1, wherein the frass is applied to the soil.

6. The method of claim 5, wherein the effective amount of the frass is applied by being worked into the soil before planting the crop.

7. The method of claim 6, wherein the effective amount of the frass is applied to the soil at least one week prior to planting the crop.

8. The method of claim 1, wherein the effective amount of the frass is applied to the crop.

9. The method of claim 1, wherein the crop is a: corn, sorghum, small grain, tobacco, sugar beet, bean, vegetable, lettuce, bok choy, or potato, grass/turf or other ornamental plant.

10. The method of claim 1, wherein the effective amount of the frass is at least about 5 tonnes per Hectare.

11. The method of claim 1, wherein the effective amount of the frass is at least about 8% dry weight frass to dry weight frass plus soil.

12. The method of claim 1, wherein the frass is applied so as to kill at least 50% of the insect pests on the crop or in the soil.

13. The method of claim 1, wherein the insect is exposed to the frass in an insect trap.

14. The method of claim 13, wherein the insect trap comprises a housing adapted to expose an insect pest to the frass.

* * * * *